United States Patent
Janik

(10) Patent No.: US 12,296,084 B2
(45) Date of Patent: May 13, 2025

(54) EXTRACORPOREAL BLOOD LINE SET AND BLOOD TREATMENT MACHINE

(71) Applicant: B. Braun Avitum AG, Melsungen (DE)

(72) Inventor: Waldemar Janik, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 677 days.

(21) Appl. No.: 17/434,045

(22) PCT Filed: Mar. 4, 2020

(86) PCT No.: PCT/EP2020/055605
§ 371 (c)(1),
(2) Date: Aug. 26, 2021

(87) PCT Pub. No.: WO2020/178301
PCT Pub. Date: Sep. 10, 2020

(65) Prior Publication Data
US 2022/0133975 A1    May 5, 2022

(30) Foreign Application Priority Data
Mar. 6, 2019  (DE) ................. 10 2019 105 655.1

(51) Int. Cl.
*A61M 1/36*        (2006.01)
*A61M 60/113*    (2021.01)
(Continued)

(52) U.S. Cl.
CPC ........ *A61M 1/3661* (2014.02); *A61M 1/3663* (2013.01); *A61M 60/113* (2021.01);
(Continued)

(58) Field of Classification Search
CPC .... A61M 1/3661; A61M 1/70; A61M 1/3663; A61M 60/113; A61M 2205/14; A61M 1/14–34
See application file for complete search history.

(56) References Cited

U.S. PATENT DOCUMENTS

| 3,807,401 A | 4/1974 | Riggle et al. |
| 4,540,406 A | 9/1985 | Miles |

(Continued)

FOREIGN PATENT DOCUMENTS

| CN | 204815048 U | 12/2015 |
| CN | 208274779 U | 12/2018 |

(Continued)

OTHER PUBLICATIONS

"Ultraschallsensor," www.wikipedia.de, Version vom, dated Feb. 26, 2019, with translation, 23 pages.
(Continued)

*Primary Examiner* — Susan S Su
*Assistant Examiner* — Erin A Kim
(74) *Attorney, Agent, or Firm* — Christopher A. Rothe; CM Law

(57) ABSTRACT

An extracorporeal blood line set for a blood treatment machine or as part of a blood treatment machine, especially a dialysis machine. The extracorporeal blood line set includes an arterial blood line having a distal patient access and a proximal device port, preferably a dialyzer port, a venous blood line having a distal patient access and a proximal device port, preferably a dialyzer port, and at least one fluid supply line which is connected to the arterial and/or venous blood line(s) in at least one port section of the arterial and/or venous blood line(s) and at one end includes a container port or a fluid container. The at least one port section is in the form of a Venturi nozzle.

10 Claims, 2 Drawing Sheets

(51) Int. Cl.
  *A61M 60/279* (2021.01)
  *A61M 60/37* (2021.01)
(52) U.S. Cl.
  CPC .......... *A61M 60/279* (2021.01); *A61M 60/37* (2021.01); *A61M 1/3672* (2013.01); *A61M 2205/14* (2013.01); *A61M 2205/3375* (2013.01)

(56) References Cited

U.S. PATENT DOCUMENTS

| | | | |
|---|---|---|---|
| 4,551,131 A | 11/1985 | Miles et al. | |
| 5,015,226 A | 5/1991 | Polaschegg | |
| 5,632,897 A | 5/1997 | Mathieu | |
| 6,131,571 A | 10/2000 | Lampotang et al. | |
| 10,420,875 B2 | 9/2019 | Beden et al. | |
| 2004/0217057 A1* | 11/2004 | Rovatti | A61M 1/1656 210/647 |
| 2009/0082676 A1 | 3/2009 | Bennison | |
| 2010/0114005 A1* | 5/2010 | Rovatti | A61M 1/3403 604/6.15 |
| 2015/0314055 A1* | 11/2015 | Hogard | A61M 1/1656 210/232 |
| 2018/0311429 A1* | 11/2018 | Janik | A61M 1/1656 |
| 2020/0069860 A1 | 3/2020 | Rammo et al. | |
| 2020/0316283 A1* | 10/2020 | Vecten | A61M 1/1621 |
| 2021/0023283 A1* | 1/2021 | Court | A61M 60/113 |

FOREIGN PATENT DOCUMENTS

| | | |
|---|---|---|
| DE | 4230513 C1 | 3/1994 |
| DE | 102011008856 A1 | 7/2012 |
| DE | 102017210134 A1 | 6/2018 |
| DE | 102017109127 A1 | 10/2018 |
| WO | 03099353 A2 | 12/2003 |
| WO | 2009030973 A1 | 3/2009 |
| WO | 2010029401 A2 | 3/2010 |

OTHER PUBLICATIONS

B. Braun: Kleiner Einsatz, grosse Wirkung Infusionsfilter von B. Braun-fuer mehr Sicherheit in der Infusionstherapie, Melsungen, dated Jan. 2013, with translation, 16 pages.
Written Opinion received in International Application No. PCT/EP2020/055605 dated Jun. 16, 2020, with translation, 10 pages.
Search Report received in German Application No. 10 2019 105 655.1 dated Nov. 29, 2019, with translation, 16 pages.
Search Report received in International Application No. PCT/EP2020/055605 dated Jun. 16, 2020, with translation, 5 pages.
Office Action received in Chinese Application No. 202080017432.7 dated Mar. 29, 2024, with translation, 16 pages.
Office Acton received in Chinese Application No. 202080017432.7 dated Jan. 5, 2024, with translation, 20 pages.
Office Action received in Chinese Application No. 202080017432.7 dated Jun. 17, 2023, with translation, 18 pages.

* cited by examiner

EXTRACORPOREAL BLOOD LINE SET AND BLOOD TREATMENT MACHINE

CROSS-REFERENCE TO RELATED APPLICATIONS

This application is the United States national phase entry of International Application No. PCT/EP2020/055605, filed Mar. 4, 2020, and claims the benefit of priority of German Application No. 10 2019 105 655.1, filed Mar. 6, 2019. The contents of International Application No. PCT/EP2020/055605 and German Application No. 10 2019 105 655.1 are incorporated by reference herein in their entireties.

FIELD

The present disclosure relates to an extracorporeal blood line set for or of a blood treatment machine, especially a dialysis machine, comprising an arterial blood line having a distal patient access and a proximal device port, preferably a dialyzer port, a venous blood line having a distal patient access and a proximal device port, preferably a dialyzer port, and at least one fluid supply line which is connected to the arterial and/or venous blood line in at least one port section of the arterial and/or venous blood line and at one end includes a container port or a fluid container.

Moreover, the present disclosure relates to an extracorporeal blood treatment machine, especially a dialysis machine, including an extracorporeal blood line set, preferably according to the invention, comprising: an arterial blood line having a distal patient access and a proximal device port, preferably a dialyzer port, between which a blood pump for delivering blood out of the patient toward the device, preferably a dialyzer, is arranged, a venous blood line having a distal patient access and a proximal device port, preferably a dialyzer port, and at least one fluid supply line which is connected to the arterial and/or venous blood line(s) in a port section of the arterial and/or venous blood line and at one end includes a container port or a fluid container.

BACKGROUND

For the extracorporeal blood treatment (e.g. hemodialysis) the blood of the patient is flushed by the so-called dialysis fluid inside the dialyzer. Accordingly, the blood is delivered through a so-called arterial tubing from the patient to the dialyzer and is subsequently returned to the patient via a venous tubing. As a rule, the blood pump is located in the arterial tubing.

Before the patient's blood enters into the dialyzer, (partially) continuously heparin or an alternative anticoagulating drug (e.g. citrate) is admixed to the patient's blood to prevent the dialyzer from clotting. This is done, for example, by a syringe pump containing the appropriate drug. The syringe pump frequently is a fixed component of the dialysis machine.

Conventional dialysis machines frequently include, for admixing the anticoagulant, a syringe pump which can be in the form of an external syringe pump or can be integrated in the dialysis machine as an integral part. Usually, the syringe pump is connected to the blood circuit via a separate tube including a Luer lock. In DE 10 2011 008 856 A1, for example, a tubing system of a dialysis machine is disclosed which has a connecting point for feeding heparin and a separate connecting point for feeding citrate. Each of the two anticoagulants is supplied to the blood tubing via a respective separate pump or syringe device.

Similarly, in DE 42 30 513 C1, a device for removing aluminum ions from blood is disclosed. In this case, too, the anticoagulant can be supplied to the blood circuit via an additional pump so as to avoid clotting of the dialyzer.

DE 10 2017 210 134 A1 in turn discloses a system for extracorporeal blood treatment. Apart from the blood pump for delivering the blood stream, in this case a second additional pump is arranged to supply the anticoagulant, especially the citrate solution, to the blood circuit.

Based on the known state of the art, the drawback of the syringe pump being a relatively complex and expensive component is evident. Moreover, the syringe pump requires very much space both inside the dialysis machine and outside the dialysis machine at the machine front end.

SUMMARY

Consequently, it is the object of the invention to avoid, or at least to alleviate, the drawbacks from the state of the art. Especially, it is intended to provide a blood line set which can administer an anticoagulant during dialysis therapy in an inexpensive and reliable manner while a conventional syringe pump is omitted. It is of particular importance for patient safety, that the anticoagulant is administered at a precisely defined rate (mass flow) even if the syringe pump is omitted.

This object is achieved, in a generic device according to a first aspect of the invention in that the at least one port section/connecting point via which the fluid supply line is connected to the arterial and/or venous blood line(s) is configured in the form of a Venturi nozzle (i.e. having a constricted flow cross-section in the blood flow path to produce a suction effect/negative pressure in the fluid flow path).

In other words, the arterial and/or venous blood line of the blood line set according to the invention comprises a section having a flow cross-section constriction, a section having a constant, constricted flow cross-section and a section having a flow cross-section expansion. According to the invention, the fluid supply line is connected to the section having the constant flow cross-section. If blood now flows through the blood line, it is accelerated via the section having the flow cross-section constriction, and the pressure in the blood line decreases. Along the section having the constant flow cross-section section, the blood flows with essentially constant (negative) pressure, so that fluid can be sucked in via the fluid supply line. Due to the constant pressure in the section having the constant flow cross-section, the suction effect and thus the delivery quantity of the anticoagulant can be exactly determined and adjusted.

This offers the advantage that the medical fluid can be supplied to the blood stream in the arterial blood line by utilizing the Venturi effect and no additional pump is required for delivering the medical solution.

Moreover, according to a second aspect of the invention, the present disclosure relates to an extracorporeal blood treatment machine, especially a dialysis machine, comprising an extracorporeal blood line set preferably according to the invention. The latter includes an arterial blood line having a distal patient access and a proximal device port, preferably a dialyzer port, a venous blood line having a distal patient access and a proximal device port, preferably a dialyzer port, and at least one fluid supply line. Between the distal patient access and the proximal device port of the arterial blood line a blood pump for delivering blood out of the patient toward the device, preferably a dialyzer, is arranged. The at least one fluid supply line is connected to the arterial and/or venous blood line in a port section/connecting point of the arterial and/or venous blood line(s) and, at one end, includes a container port or a fluid container. Accordingly, a fluid supply line valve unit is disposed between the at least one port section and the container port or the fluid container. Said fluid supply line valve unit is configured for regulating or controlling the fluid supply flow which is caused exclusively by using a suction pressure (negative pressure) in the fluid supply line generated by the blood stream in the arterial and/or venous blood line(s). The blood treatment machine according to the invention thus permits controllable supply of a medical fluid into the blood stream without an additional pump being required.

In a preferred configuration, the port section/connecting point may be arranged downstream of the pump between the pump and the device at the arterial blood line.

In another configuration, the port section may as well be arranged upstream of the pump between the patient access and the pump at the arterial blood line. When the port section is arranged at this point, the port section may also be a T piece of substantially constant cross-section in the blood flow direction, which helps to reduce the production cost during manufacturing of the port section.

In a preferred configuration, the control device may control the fluid supply line valve unit on the basis of the blood stream, the pressure of the blood stream and a target flow rate of a medical fluid stored in the fluid container by opening the fluid supply line valve unit for a predetermined opening time and at a predetermined opening frequency. Thus, the flow rate and, resp., the admixing quantity of the medical fluid can be precisely controlled. The control device can define the opening time and the opening frequency by using a coding, especially a Barker code. In a preferred configuration, a Barker code of the length three with the coding "+1 +1 −1" can be used, wherein "+1" may stand for a comparatively long opening time of the valve with a short opening frequency and, resp., a long periodic time and, on the other hand, "−1" may stand for a shorter opening time with a higher opening frequency and, resp., a shorter periodic time.

According to the invention, the blood treatment machine may have a detection unit which detects a connecting state of the fluid supply line with the fluid supply line valve unit and, depending on the detection result, outputs for example an optical, acoustic or capacitive signal. In this way, a lacking insertion of the fluid supply line and accompanying permanent opening of the fluid supply line valve unit can be detected and an inadvertently high administration of the medical fluid which possibly endangers the patient can be prevented.

In another configuration according to the invention, at the fluid supply line a, preferably non-invasive, flow rate sensor, especially an ultrasonic sensor, can be disposed for determining a solution flow rate within the fluid supply line. The ultrasonic sensor may be formed integrally with the fluid supply line valve unit and may equally detect the solution flow rate and the connecting state of the fluid supply line with the fluid supply line valve unit. The arrangement of the flow rate sensor permits exact monitoring of the flow rate of the medical fluid, and the integration of the flow rate monitoring and of the connecting state detection allows to reduce the number of components and the system complexity. In addition, the positioning of the flow rate sensor also offers the advantage that air can be detected in the fluid supply line and thus possible running empty of a container storing the medical fluid can be detected.

In accordance with the invention, a filter unit, especially a so-called air stop filter, which prevents air from flowing into the fluid supply line may be additionally disposed at the fluid supply line. The filter unit may either be integrated as a fixed part in the fluid supply line or may be configured as a separate intermediate piece.

As an alternative to the position of the flow rate sensor at the fluid supply line, in another configuration according to the invention, the flow rate sensor may be located downstream of the connecting point at the arterial blood line. Accordingly, the flow rate can be monitored by using a difference of a first blood flow rate and a second blood flow rate with consideration of the opening time of the fluid supply line valve unit. When the fluid supply line valve unit is closed, the flow rate sensor can measure the first blood flow rate and, when the fluid supply line valve unit is opened, the flow rate sensor can measure the second blood flow rate. This offers the advantage that the flow rate sensor can also be used, apart from determining the flow rate of the fluid, for detecting air which is possibly contained in the blood stream.

In another configuration according to the invention, the connecting point may be adapted to be disposed at the arterial blood line via a detachable connection, especially a Luer lock connection. The connecting point including the fluid supply line in this case is in the form of a separate component, which offers the advantage that conventional line sets need not be modified.

As an alternative to the fluid supply line valve unit, which can be operated merely in the closed state and the open state, in a configuration according to the invention also a proportional valve may be used which can control the flow rate of the medical fluid by arbitrarily precise variation of the cross-sectional area of the fluid supply line.

BRIEF DESCRIPTION OF THE DRAWING FIGURES

DETAILED DESCRIPTION

Figure 1:
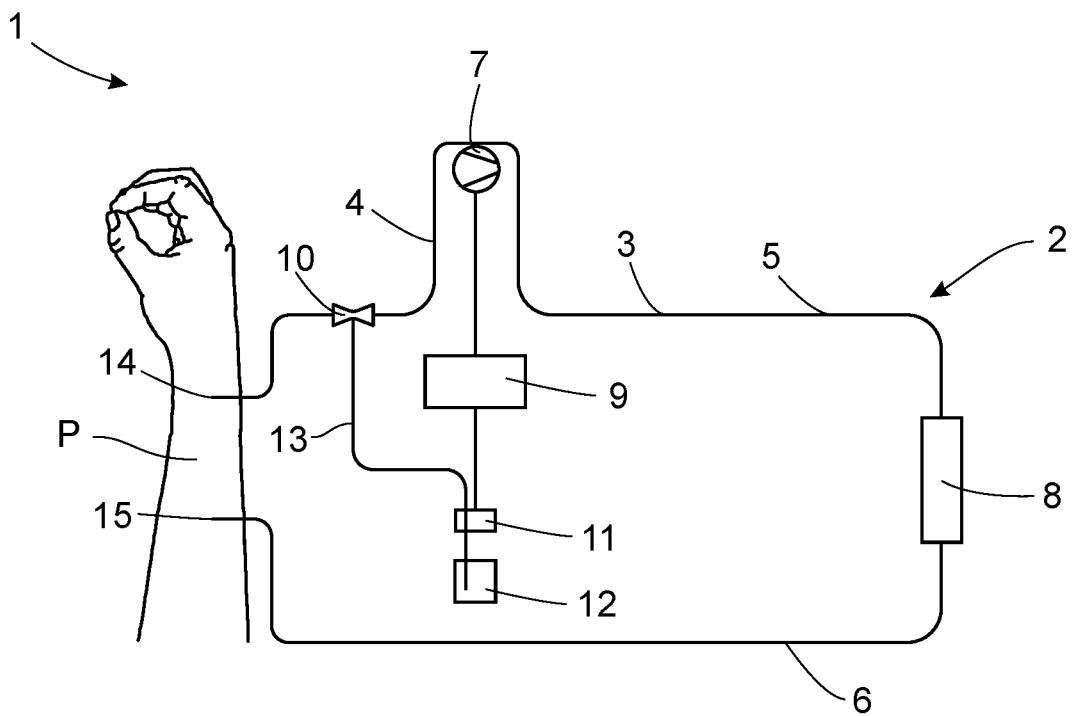
FIG. 1 is a representation to illustrate a system structure of a dialysis machine according to a first embodiment of the present disclosure.

Hereinafter, embodiments of the present disclosure will be described on the basis of the related figures. Like elements are provided with like reference numerals. The features of the individual embodiments may be interchanged.

First Embodiment

FIG. 1 shows a representation to illustrate a schematic structure of a dialysis machine 1 comprising an extracorporeal blood line set 2 according to a first embodiment of the present disclosure. The line set 2 includes an arterial blood line 3 which comprises a first arterial blood line portion 4 and a second arterial blood line portion 5, a venous blood line 6, a pump 7, a dialyzer 8, a control device 9, a branching point/connecting point/port section 10, a valve 11, a container 12 and a fluid supply line 13. The dialyzer 8 in this case is an example of "a device" and serves for purifying the blood of a patient P.

At one end of the first arterial blood line portion 4 there is formed a line set inlet 14 via which the blood of the patient P to be purified flows into the line set 2 and which corresponds to a first patient access. The other end of the first arterial blood line portion 4 is connected to an inlet side of the pump 7 and, resp., is in pump engagement. An outlet side of the pump 7 is connected to one end of the second arterial blood line portion 5. In the case of a rotor/peristaltic pump common for blood pumps, the arterial blood line 3 may also be looped or threaded into the blood pump 7, which results in the first and second arterial blood line portions 4, 5 (in one piece). The other end of the second arterial blood line portion 5 is connected in turn to an inlet of the dialyzer 8. An outlet of the dialyzer 8 is in communication with one end of the venous blood line 8. Via a line set outlet 15 being formed at the other end of the venous blood line 6 and corresponding to another patient access, the purified blood is supplied to the patient P again. The ports via which each of the second arterial blood line portion 5 and the venous blood line 6 is connected to the dialyzer 8 are in the form of so-called Luer locks in the preferred embodiment.

In the preferred embodiment, the pump 7 is a peristaltic pump so that the patient's blood is delivered from the patient P to the dialyzer 8 due to the rotation of the pump 7. When the pump 7 is operated on the basis of a control command of the control device 9, in the first arterial blood line portion 4 a negative pressure is forming so that the blood of the patient P to be purified is sucked in and flows into the first arterial blood line portion 4 via the line set inlet 14. The pump 7 delivers the blood through the second arterial blood line portion 5 toward the dialyzer 8. In the dialyzer 8, a dialyzing fluid purifies the blood while circulating around the same. The operation of the pump 7 causes excess pressure to form in the blood flow direction downstream of the pump 7 in the second arterial blood line portion 5, the dialyzer 8 and the venous blood line 6, said excess pressure causing the blood to flow from the pump 7 through the second arterial blood line portion 5, the dialyzer 8 and the venous blood line 6 back to the patient P.

Figure 2:
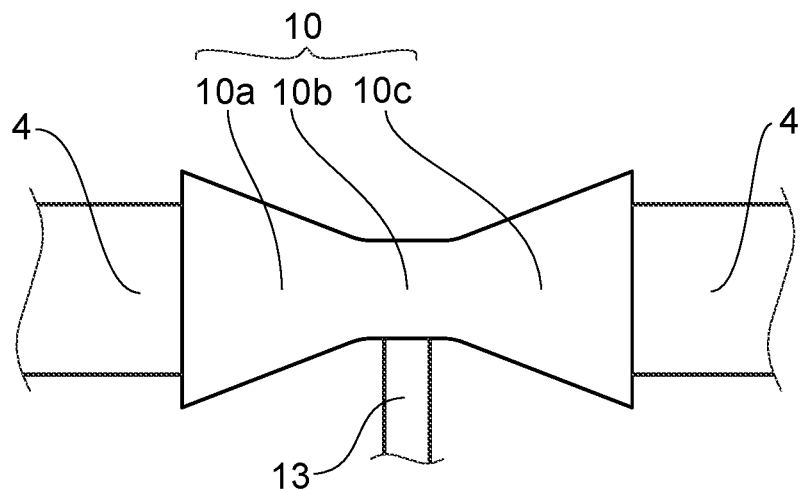
FIG. 2 is a schematic detailed view of a connection section of the dialysis machine according to the first embodiment.

Moreover, in the extracorporeal line set 2 the connecting point 10 is formed. Said connecting point 10 is arranged, in the first embodiment, between the line set inlet 14 and the pump 7 at the first arterial blood line portion 4 and is substantially in the form of a Venturi tube/a Venturi nozzle so that a cross-section of the connecting point 10 decreases along the blood flow direction. At a point where the cross-section of the connecting point 10 is minimal, one end of the fluid supply line 13 is disposed to branch off. The connection point 10 according to the first embodiment is schematically shown in FIG. 2. As can be seen therein, the connection point 10 designed in the form of the Venturi nozzle has, in the direction of flow, a flow cross-section constriction section 10a, a section having a constant flow cross-section 10b and a flow cross-section expansion section 10c, the flow cross-section constriction section 10a and the flow cross-section expansion section 10c each being connected to the first arterial blood line section 4. At the section having the constant flow cross-section 10b, the fluid supply line 13 is connected. When blood flows through the first arterial blood line section 4 into the connection point 10 it is accelerated via the flow cross-section constriction section 10a. Due to this acceleration, the pressure in the blood flow decreases. Thus, along the section having the constant flow cross-section 10b, the blood flows at a constant negative pressure.

The other end of the fluid supply line 13 is connected to the container 12 in which an anticoagulant is stored. The anticoagulant in this case is an example of "a medical fluid". When the pump 7 is operated, as described before, the blood flows through the line set 2 and, due to the configuration of the connecting point 10 and the resulting Venturi effect, the anticoagulant is sucked from the container 12 to the connecting point 10 and finally into the first arterial blood line portion 4. Apart from the Venturi effect, also due to the above-described negative pressure prevailing in the first arterial blood line portion 4, the anticoagulant flows from the container 12 via the connecting point 10 into the first arterial blood line portion 4.

Between the connecting point 10 and the container 12, the valve 11 is arranged at the fluid supply line 13. The valve 11 is an example of "a fluid supply line valve unit" here and is arranged to release or inhibit the flow of the anticoagulant from the container 12 toward the connecting point 10 in response to a control command of the control device 9 by opening or closing the valve 11. In the first embodiment, the valve 11 is a squeeze valve.

In other words, FIG. 1 exemplifies the patient P from whom blood flowing through the blood line 3 to the dialyzer 8 is withdrawn through the arterial blood line 3 by means of the pump 7. After being purified in the dialyzer, the blood is delivered back to the patient P through the venous blood line 6. In the arterial blood line 3 there is provided the connecting point 10 to which the fluid supply line 13 is attached. The fluid supply line 13 leads to the container 12 which contains the anticoagulant. The element 11 is configured as a valve 11, preferably a squeeze valve or clamp, and enables or inhibits the transport of the anticoagulant through the fluid supply line 13. In other words, the flow of the anticoagulant can be regulated by means of the valve 11. The connecting point 10 includes the cross-sectional change in the direction of blood flow. At the narrowest point, the fluid supply line 13 is placed to branch off. According to the Venturi principle, the anticoagulant is sucked through said fluid supply line 13 out of the container 12 as soon as the blood flows through the arterial blood line 3. In addition to the Venturi effect, during suction of the anticoagulant also the negative pressure in the arterial blood line 3 caused by the pump 7 matters.

In the line set 2 according to the first embodiment, in addition there is integrally arranged on the valve 11 a detection unit in the form of an ultrasonic sensor 16 (not shown in FIG. 1) which optically detects a connection state of the fluid supply line 13 with the valve 11 and, based on the detected connection state of the fluid supply line 13 with the valve 11, outputs a signal. The ultrasonic sensor 16 is connected to the control device 9. When the fluid supply line 13 is not correctly connected to the valve 11, the ultrasonic sensor 16 outputs the signal to the control device 9 which then closes the valve 11 and/or stops the pump 7 so as to prevent inadvertently high administration of the anticoagulant which might endanger the patient. The ultrasonic sensor 16 is only an example of "a detection unit" here.

In other words, in order to ensure safe and correct administration of the anticoagulant the squeeze valve 11 may include in its holding fixture for the fluid supply line 13 a detection unit which can detect e.g. optically, acoustically or capacitively whether the fluid supply line 13 has been correctly inserted. Otherwise, a lack of insertion of the fluid supply line 13 would be tantamount to a permanent opening of the valve 11, which would entail the inadvertently high administration of the anticoagulant which might endanger the patient.

For monitoring the correct administration of the anticoagulant, the ultrasonic sensor 16 in the first embodiment is arranged to determine, in addition to the detection of the connection state, a flow rate of the anticoagulant in the fluid supply line 13 non-invasively, for example in the form of measurement of delay time difference.

When the ultrasonic sensor 16 is formed integrally with the valve 11, said sensor can also detect air within the fluid supply line 13. When the anticoagulant has completely flown out of the container 12 after a certain period of time due to the operation of the pump 7, air can be sucked into the fluid supply line 13. In order to prevent air infusion into the blood of the patient P, the control device 9 closes the valve 11 as soon as the ultrasonic sensor 16 detects air within the fluid supply line 13. Alternatively, or additionally, then also the pump 7 can be stopped.

In other words, the invention according to the first embodiment provides determining the flow of the anticoagulant. Of preference, this is achieved by non-invasive flow measurement at the fluid supply line 13. In this case, ultrasonic flow measurement in the form of a measurement of delay time difference is imaginable. The ultrasonic sensor 16 is integrated in the valve 11. In this case, the valve 11 takes over the following tasks:

receiving the fluid supply line 13
squeezing the fluid supply line 13
detecting the fluid supply line 13
determining the flow inside the fluid supply line 13.

In the first embodiment, thus the ultrasonic sensor 16 is used both for the flow determination and for the detection of the connection state. The ultrasonic sensor 16 attached to the fluid supply line 13 moreover offers the advantage that thus also air within the fluid supply line 13 can be detected. When the container 12 runs empty, the ultrasonic sensor 16 detects air inside the fluid supply line 13, whereupon the valve 11 will close and thus air infusion is prevented.

As already described above, in the first embodiment the flow rate of the anticoagulant is controlled by the control device 9 by periodically opening and closing the valve 11. The valve 11 additionally includes, in the first embodiment, a resilient element which maintains the valve 11 in the closed state, unless there is a control command from the control device 9. When the control device 9 determines that the valve 11 is to be opened, an actuator is moved, preferably electromagnetically, against the restoring force of the resilient element so that the valve 11 opens.

In the first embodiment, the control device 9 controls the flow volume of the anticoagulant on the basis of the set pump performance of the pump 7 by controlling an opening time and an opening frequency of the valve 11. Here the product from the opening time and the opening frequency of the valve 11 is proportional to the flow rate of the anticoagulant through the fluid supply line 13.

In other words, the addition of the anticoagulant from the container 12 through the fluid supply line 13 is performed periodically and pulsed, according to the invention, by opening the valve 11 for a short time. The flow rate/ admixing quantity depends on the set blood stream of the pump 7 as well as on the opening time and the opening frequency of the valve 11. The product of the opening time and the opening frequency is referred to as pulse-duty factor which in turn is proportional to the admixing quantity. Moreover, also the pressure prevailing in the first arterial blood line portion 4 is possibly important so that, according to the present invention, said pressure can be equally taken into account. Pressure measurements are already made at conventional dialysis machines in the blood lines 4, 5 and 6 so that the pressure can be easily used to precisely adjust the admixing rate. Further, the valve 11 as a standard is closed by a spring restoring force to prevent the anticoagulant from being permanently sucked. Admixing is controlled by the control device 9 with consideration of the blood stream, the pressure and the target flow rate of the anticoagulant.

In order to detect deviation from proper function of the valve 11, the anticoagulant is added in coded form. In the first embodiment, a Barker code of the length three with "+1 +1 −1" is predetermined by the control device 9 and is used to control the valve 11. Accordingly, "+1" stands for a comparatively long opening time of the valve 11 with short opening frequency and, resp., long periodic time. On the other hand, "−1" stands for a shorter opening time with higher opening frequency and, resp., shorter periodic time, wherein in both cases the pulse-duty factor is equal and thus the admixing quantity of the anticoagulant is not varied.

During operation, in the flow measurement the ultrasonic sensor 16 detects, as mentioned above, a flow sequence and compares the same to the predetermined Barker code. When the valve 11 works properly, the detected flow sequence corresponds to the Barker code.

In other words, when the valve 11 additionally includes the ultrasonic sensor 16 for flow measurement, the aforementioned Barker code must equally be detectable when the valve 11 is functional. This means for "+1 +1 −1": "long flow, long flow, short flow".

In the first embodiment, the fluid supply line 13 is initially automatically filled when it is connected to the line set 2 so as to avoid air infusion in the port during therapy. At best, this occurs during so-called priming by opening the valve 11 which pursues the objective to render the blood line set 2 free from air before it is connected to the patient P.

Modification of the First Embodiment

Figure 3:
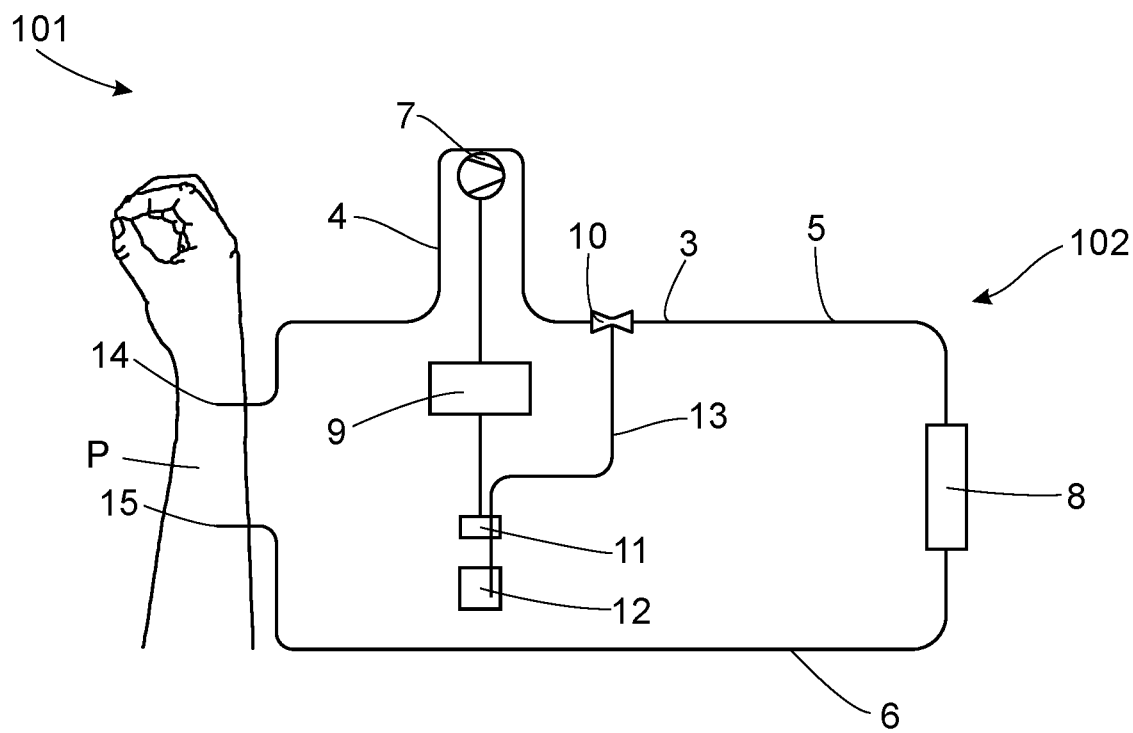
FIG. 3 is a representation to illustrate a system structure of a dialysis machine according to a modification of the first embodiment of the present disclosure.

Hereinafter, a modification of the first embodiment will be described with respect to FIG. 3. FIG. 3 illustrates a structure of a dialysis machine 101 comprising a modified extracorporeal blood line set 102. The structure and the functioning of the modified line set 102 substantially corresponds to the extracorporeal blood line set 2 according to the first embodiment; therefore, description thereof will not be repeated and in the following merely the differences shall be illustrated.

As is evident from FIG. 3, in the line set 102 according to the modification of the first embodiment the connecting point 10 is arranged at the second arterial blood line portion 5 between the pump 7 and the dialyzer 8. When the connecting point 10 is arranged in the blood flow direction downstream of the pump 7, merely due to the Venturi effect the anticoagulant flows from the container 12 to the connecting point 10 and into the second arterial blood line portion 5.

In the modified first embodiment, consequently the flow volume of the anticoagulant is controlled, in contrast to the first embodiment in which the pressure prevailing in the first arterial blood line portion 4 is taken into account, in response to the pressure prevailing in the second arterial blood line portion 5.

In other words, an alternative position for the Venturi nozzle 10 is provided in the second arterial blood line portion 5. Since the nozzle 10 is placed downstream of the pump 7 here, in the area of the second arterial blood line portion 5 in which the nozzle 10 is placed, excess pressure is prevailing so that the suction of the anticoagulant from the container 12 through the fluid supply line 13 is caused exclusively by the Venturi effect.

Second Embodiment

Figure 4:
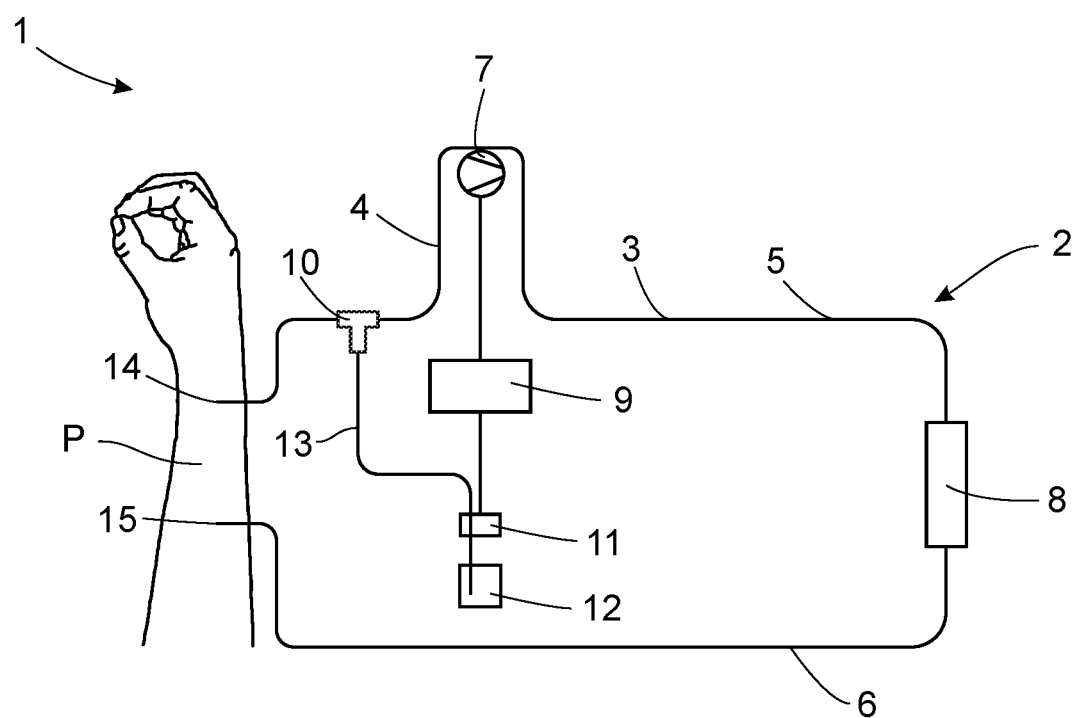
FIG. 4 is a representation to illustrate a system structure of a dialysis machine according to a second embodiment of the present disclosure.

Hereinafter, a dialysis machine 201 according to a second embodiment as set forth in the present disclosure, which is shown in FIG. 4, is described. The structure and the functioning of the dialysis machine 201 substantially corresponds to the dialysis machine 1 according to the first embodiment; therefore, description thereof will not be repeated and hereinafter merely the differences will be illustrated.

In the second embodiment, the connecting point/port section 210 is configured, in contrast to the first embodiment, as a simple T piece of substantially constant cross-section in the blood stream direction. The fluid supply line 13 is arranged to branch off so that the medical fluid can be supplied to the blood stream. When the connecting point 210 according to the second embodiment is in the form of a T piece, the connecting point 210 must be arranged in the first arterial blood line portion 4. Accordingly, the fluid is sucked merely due to the negative pressure generated by the pump 7 in the first arterial blood line portion 4 from the container 12 through the fluid supply line 13 into the first arterial blood line portion 4.

In other words, when the Venturi nozzle is located in the arterial first blood line 4, the nozzle may also be in the form of a simple T piece so that solely the vacuum by the pump 7 effectuates suction.

The present invention has been described by way of exemplary configurations in the foregoing. However, the present invention is not restricted thereto.

In the first embodiment and the modification of the first embodiment, the nozzle-shaped connecting point 10 is a fixed part of the line set 2 in the arterial blood line 3. However, the connecting point 10 including the fluid supply line 13 may be in the form of an additional separate component (disposable). In this way, the connecting point 10 may be arranged, for example, between the second arterial blood line portion 5 and the dialyzer 8 via a Luer lock. This offers the advantage that conventional line sets need not be modified.

Moreover, in the afore-described embodiments the valve 11 is a valve having merely a closed state and an open state. As an alternative to said valve 11 having only two states, also a proportional valve may be used, however. The latter can vary the cross-section of the fluid supply line 13 and thus control the flow rate of the anticoagulant preferably by any precise squeezing of a portion of the fluid supply line 13. Accordingly, it is not the concrete design of the valve 11, but merely the fact that with the aid thereof the flow of the anticoagulant through the fluid supply line 13 can be regulated, which is relevant to the invention.

In the afore-described embodiments, the ultrasonic sensor 16 is arranged as flow rate sensor at the fluid supply line 13. However, any other non-invasive sensor can also be used to detect the flow rate. In addition, in the afore-described embodiments, the ultrasonic sensor 16 is arranged as flow rate sensor at the fluid supply line 13. Alternatively, the flow rate sensor may also be located in the blood stream direction downstream of the connecting point 10 of the anticoagulant at the arterial blood line 3. Without addition of the anticoagulant the sensor measures a first blood flow rate. Upon addition of the anticoagulant, the sensor 16 measures a second blood flow rate. The difference of the first and second blood flow rates shows the flow rate of the anticoagulant out of the container 12 with consideration of the time of admixing. Furthermore, the admixing quantity of the anticoagulant could also be established by means of a filling level sensor within/at the container 12 or by monitoring the weight of the container 12.

In the afore-described embodiments, the ultrasonic sensor 16 serves as detection unit for detecting the connection state between the fluid supply line 13 and the valve 11. The detection unit may also be in the form of a, for example optical, acoustic or capacitive, separate detection unit.

Further, in the afore-described embodiments, the ultrasonic sensor 16 is formed integrally on the valve 11 at the fluid supply line 13. Alternatively, the ultrasonic sensor 16 may as well be arranged as a separate sensor device.

In the afore-described embodiments, the ultrasonic sensor 16 is used to detect running empty of the container 12. It is imaginable in addition or as an alternative to provide the fluid supply line 13 with a so-called air stop filter. Said filters are sufficiently known from infusion technology and there prevent infusion systems from running empty. Such filter may be located between the fluid supply line 13 and the container 12. It may either be a fixed part of the fluid supply line or a separate intermediate piece.

For monitoring the proper admixing of the anticoagulant, in the afore-described embodiments a Barker code of the length three is used. However, also Barker codes of different length or other types of coding can be used, as a matter of course.

It is pointed out that, although further common elements are not depicted in FIG. 1, FIG. 3 and FIG. 4, they are still taken into account by the invention. These include e.g. air detectors, air traps, admixing and withdrawing points, clamps and, resp., valves, non-optical sensors (e.g. pressure sensors) and optical sensors (e.g. for hematocrit determination).

The invention claimed is:

1. An extracorporeal blood treatment machine having an extracorporeal blood line set, the extracorporeal blood treatment machine comprising:
    an arterial blood line having a first distal patient access, a first proximal device port, and a blood pump arranged between the first distal patient access and the first proximal device port, the blood pump for delivering blood from a patient to a device,
    a venous blood line having a second distal patient access and a second proximal device port,
    at least one fluid supply line which is connected to the arterial blood line in a port section of the arterial blood line, the at least one fluid supply line arranged upstream of the blood pump and including a fluid container at one end, and
    a fluid supply line valve unit between the port section and the fluid container which fluid supply line valve unit is configured to regulate or control a fluid supply flow which is effectuated exclusively using a suction pressure in the at least one fluid supply line generated by a blood stream in the arterial blood line.

2. The extracorporeal blood treatment machine according to claim 1, further comprising a control device which is arranged to control the fluid supply line valve unit based on a blood stream, a pressure of the blood stream and a target flow rate of a medical fluid stored in the fluid container, the control device controlling the fluid supply line valve unit by opening the fluid supply line valve unit for an opening time and at an opening frequency.

3. The extracorporeal blood treatment machine according to claim 2, wherein the control device determines the opening time and the opening frequency by using a coding.

4. The extracorporeal blood treatment machine according to claim 1, wherein the fluid supply line valve unit includes a detection unit which detects a connection state of the at least one fluid supply line with the fluid supply line valve unit and, in response to a detection result, outputs a signal when the at least one fluid supply line is not connected to the fluid supply line valve unit.

5. The extracorporeal blood treatment machine according to claim 1, wherein the port section comprises a flow cross-section constriction section and a flow cross-section expansion section, wherein the flow cross-section expansion section is downstream of the flow cross-section constriction section in a direction of flow from the first distal patient access to the blood pump.

6. The extracorporeal blood treatment machine according to claim 5, wherein the at least one fluid supply line has an outlet in fluid communication between the flow cross-section constriction section and the flow cross-section expansion section.

7. The extracorporeal blood treatment machine according to claim 5, wherein the port section comprises a constant flow cross-section portion between the flow cross-section constriction section and the flow cross-section expansion section.

8. The extracorporeal blood treatment machine according to claim 7, wherein the at least one fluid supply line has an outlet in fluid communication at the constant flow cross-section portion.

9. The extracorporeal blood treatment machine according to claim 3, wherein the coding comprises a Barker coding.

10. The extracorporeal blood treatment machine according to claim 9, wherein the Barker coding comprises a length three with a coding "+1+1 −1," wherein "+1" designates a first opening time, and "−1" designates a second opening time that is shorter than the first opening time.

* * * * *